United States Patent
Ketre Kolukirik et al.

(10) Patent No.: US 12,220,113 B2
(45) Date of Patent: Feb. 11, 2025

(54) TUBE STRUCTURE USED IN MOLECULAR DIAGNOSTIC SYSTEMS

(71) Applicant: IVD Biyoteknoloji Sanayi Ticaret Anonim Sirketi, Istanbul (TR)

(72) Inventors: Canan Zöhre Ketre Kolukirik, Istanbul (TR); Lütfi Erzurumlu, Istanbul (TR); Mustafa Kolukirik, Istanbul (TR); Ömür Baç, Istanbul (TR)

(73) Assignee: BIOEKSEN AR GE TEKNOLOJILERI ANONIM SIRKETI, Istanbul (TR)

( * ) Notice: Subject to any disclaimer, the term of this patent is extended or adjusted under 35 U.S.C. 154(b) by 0 days.

(21) Appl. No.: 17/791,408

(22) PCT Filed: Apr. 30, 2021

(86) PCT No.: PCT/TR2021/050417
§ 371 (c)(1),
(2) Date: Jul. 7, 2022

(87) PCT Pub. No.: WO2022/231537
PCT Pub. Date: Nov. 3, 2022

(65) Prior Publication Data
US 2024/0197296 A1    Jun. 20, 2024

(51) Int. Cl.
*A61B 10/00* (2006.01)
(52) U.S. Cl.
CPC .................. *A61B 10/0096* (2013.01)

(58) Field of Classification Search
CPC ...... B01L 3/502; B01L 3/5021; B01L 3/5023; B01L 3/50; A61B 10/0045; A61B 10/0096
See application file for complete search history.

(56) References Cited

U.S. PATENT DOCUMENTS

| | | | |
|---|---|---|---|
| 6,312,395 B1 * | 11/2001 | Tripp ................ | A61B 10/0045 600/572 |
| 2004/0267181 A1 * | 12/2004 | Tuite ..................... | A61B 10/02 604/1 |
| 2005/0023182 A1 * | 2/2005 | Shah .................... | B01L 3/5021 206/570 |

FOREIGN PATENT DOCUMENTS

| CN | 106053121 A | * 10/2016 | ............... G01N 1/02 |
|---|---|---|---|
| CN | 208171629 U | * 11/2018 | |

OTHER PUBLICATIONS

International Search Report and Written Opinion of the International Searching Authority for corresponding PCT/TR2021/050417, dated Jan. 19, 2022.

\* cited by examiner

*Primary Examiner* — Javier A Pagan
(74) *Attorney, Agent, or Firm* — Egbert, McDaniel & Swartz, PLLC

(57) ABSTRACT

Disclosed is a tube structure with a cap which is used to transport a respiratory tract agent sample after it is taken. The tube structure has a body specially designed for a swab rod structure, and a cavity formed inside the body according to the swab rod structure.

1 Claim, 3 Drawing Sheets

TUBE STRUCTURE USED IN MOLECULAR DIAGNOSTIC SYSTEMS

FIELD OF THE INVENTION

The present invention relates to a viral transport medium/tube structure used as a part of the molecular diagnostic systems for transporting the sample taken at the phase of transport after sampling of respiratory tract agents in the molecular biology field.

STATE OF THE ART

Today, molecular diagnosis can be performed using various methods. Molecular diagnosis applications made with Polymerase Chain Reaction (PCR) consist of three main steps. The first step is sampling from the patient, the second step is the extraction of nucleic acids and the third step is the polymerase chain reaction.

The first step is sampling from the patient. At this step, different sample types such as blood, serum, throat swab, stool etc. are used according to the type of agent to be studied. Mainly samples taken from the throat and nose are used in determining the respiratory tract agents. The most widely used sample type is nasopharyngeal swab sample with the highest viral load collection capacity. The swab samples must be collected from the nasopharynx at the back of the nose and throat so as to collect nasopharyngeal sample type from the patient. Sterile long, thin rods made of ABS material called swabs are used so as to collect samples from the nasopharynx. The rods used are completely with synthetic tips (dacron/rayon/nylon flocked) and sterile. Furthermore, the swab rod is very thin due to the region where swab sample is taken.

The patient samples collected with the used swab rods are placed in a transport tube/viral transport medium and sent to the relevant center for nucleic acid extraction. The swab rods are approximately 180-200 mm long and 60-80 mm of them are in temporary contact with the nose/throat area during the collection of the swab, then this section is broken into the tube and the samples are taken into the transport tube by using straight tubes of approximately 90-100 mm length.

The swab rod used in the application is broken from the section covering the contact areas after the application and located into the viral transport medium/tube and is not removed anymore. The 13-25 mm part located at the tip of the swab rod is the section where the patient sample is intensively collected, there is fluid in the viral transport medium/tube that allows nucleic acids to be transported in accordance with the PCR process up to the region including the tip of the swab rod that serves to collect sample. When the currently used diameters and length of viral transport medium/tubes are taken into account, there must be at least 2 ml to 2.5 ml of liquid so as to transport the tip section carrying sample within the tube without drying.

When the samples in the tube are sent to the center where the PCR process is performed in the current method (swab rod application), 5 ul of liquid should be pipetted from the viral transport medium/tube so as to establish a reaction during the use of PCR diagnostic kits. It is appropriate to use a 10 ul pipette tip so as to perform pipetting of 5 ul liquid containing patient sample. The length of the pipette tips changes due to the amount of liquid they carry, and the length of the 10 ul pipette tip is about 30 mm.

5 ul of liquid cannot be pipetted directly from the sample transport medium/tube by attaching a 10 ul pipette tip to the pipette so as to maintain PCR reaction. Both the 30 mm long 10 ul pipette tip cannot reach the liquid at the bottom of the tube, and if the pipette contacts the walls of the tube, there is a risk of contamination in the laboratory. Thus, first of all 1000 ul pipette tip is attached to the pipette and a volume higher than 5 ul of the liquid in the sample transport tube is taken into an empty container by using a 1000 ul pipette tip. Transferring 5 ul liquid to the PCR process directly with a 1000 ul pipette tip cannot be performed since the sensitivity of the 1000 ul pipette tip is not appropriate. Subsequently, in order to pipette 5 ul of the liquid containing viral load taken into another container, 10 ul pipette tip is attached to the pipette and appropriate volume for PCR process is carried out by pipetting the liquid containing 5 ul viral load.

Problems that occur in the state of the art are as follows:
  Using a long (80-100 mm) virus transport medium/tube is required because the broken part of the swab rod with nasopharyngeal swab inside the tube is long. The virus transport medium should contain 2 ml-2.5 ml liquid for retaining the sampling section at the end of the swab rod in the liquid. Here, 2 ml-2.5 ml liquid creates a disadvantage in terms of both the cost of viral transport medium production and decrease in the virus concentration.
  Liquid is taken from the bottom with a 1000 ul pipette tip and carried to a container since viral transport medium/tube is long and then PCR setup is made with a 10 ul pipette tip. Herein, a further pipette tip and a further empty container are used for each process carried out with the existing system.
  Intermediate processes extend the duration of the process, it causes more labor costs.
  The risk of sample contamination increases during intermediate processes.
  Contamination risk of the personnel performing the processes increases during intermediate processes.

As a result of the research made on the subject, a similar application is not encountered.

As a result due to the abovementioned disadvantages and the insufficiency of the current solutions regarding the subject matter, a development is required to be made in the relevant technical field.

AIM OF THE INVENTION

The invention aims to solve the abovementioned disadvantages by being inspired from the current conditions.

The main aim of the invention is to design the tube in a thin and long formed structure that is slightly larger than the diameter of the sample collection section in the tip section of the swab rod and to make it more compatible with the swab rod.

Another aim of the invention is to reduce the volume required in the tube from 2 ml of liquid to 1 ml of liquid with the design of the tube structure.

Another aim of the invention is to reduce both the cost and the virus concentration by reducing the volume required in the tube from 2 ml to 1 ml.

Another aim of the invention is to obtain a liquid level in the tube that can be directly pipetted with a 10 ul pipette tip with the design of the tube structure.

Another aim of the invention is to eliminate the two-phase pipetting processes and related problems that arise in the state of the art with the design of the tube structure.

Another aim of the invention is to eliminate further usage of a pipette tip and an empty container for each sample and for each processes carried out with the existing system.

Another aim of the invention is to decrease duration of intermediate processes and labor cost.

Another aim of the invention is to decrease contamination risk during the processes.

Another aim of the invention is to decrease contamination risk of the personnel performing the processes during intermediate processes.

The structural and characteristic features of the present invention will be understood clearly by the following drawings and the detailed description made with reference to these drawings and therefore the evaluation shall be made by taking these figures and the detailed description into consideration.

FIGURES CLARIFYING THE INVENTION

DESCRIPTION OF THE PART REFERENCES

10. Tube structure
11. Cap
12. Sealing element
13. Body
14. Gap
20. Swab rod

DETAILED DESCRIPTION OF THE INVENTION

In this detailed description, the preferred embodiments of the inventive tube structure (10) are described by means of examples only for clarifying the subject matter.

Figure 1:
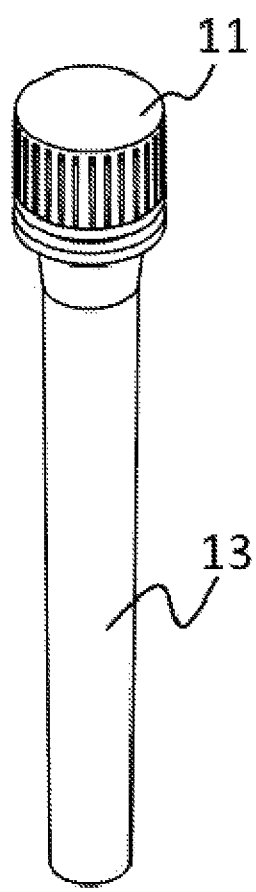
FIG. 1, is a perspective view of the inventive tube structure.
Figure 2:
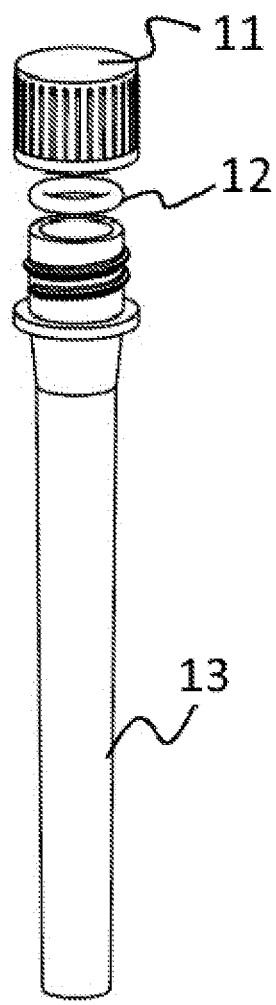
FIG. 2, is a perspective disassembled view of the inventive tube structure.

The tube structure (10) consisting of three parts in total is shown in FIG. 1 and FIG. 2. The screw cap (11) is used by being assembled with the sealing element (12) attached inside it. The cap (11) has a screwed mechanism. The sealing element (12) is used inside the cap (11) so as to provide sealing.

The present invention relates to a tube structure (10) with a cap (11) which is used to transport the respiratory tract factor sample after it is taken. The tube structure (10) distinctively comprises a body (13) specially designed for the swab rod (20) structure and a cavity (14) formed inside the body (13) according to the swab rod (20) structure.

Figure 3:
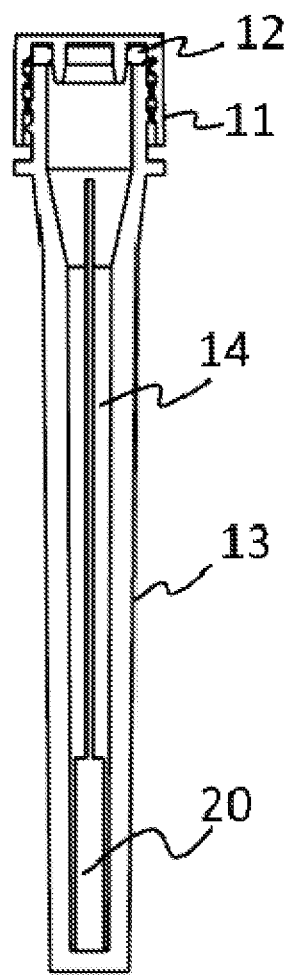
FIG. 3, is a sectional view of the inventive tube structure.

The use of the swab rod (20) in the tube configuration is shown in FIG. 3. The body (13) is used to carry the viral load with the swab. The cavity (14) ensures to always keep the parts of the swab rod (20) with viral load in the transport fluid. Therefore, direct pipetting can be made during the PCR configuration phase.

The swab rod (20) is broken and located into the cavity (14) in the body (13) after the nasopharyngeal swab sample is taken. The tube structure (10) whose cap (11) is closed can transport the liquid it contains without leakage.

The invention claimed is:

1. An assembly for transporting a respiratory tract factor sample, the assembly comprising:
    a swab rod having a swab at an end thereof;
    a tubular structure having a body with a cavity formed therein, said swab rod being removably received in the cavity, the cavity having a constant diameter slightly larger than a diameter of the swab in an area adjacent the swab;
    a liquid received in the cavity around the swab, the liquid having a volume of approximately one milliliter, said liquid adapted to receive the respiratory tract factor sample; and
    a cap threadedly secured to an end of said tubular structure.

* * * * *